North American Patent [19]

Sramek

[11] Patent Number: 4,807,638
[45] Date of Patent: Feb. 28, 1989

[54] NONINVASIVE CONTINUOUS MEAN ARTERIAL BLOOD PRSSURE MONITOR

[75] Inventor: Bohumir Sramek, Irvine, Calif.

[73] Assignee: Bomed Medical Manufacturing, Ltd., Irvine, Calif.

[21] Appl. No.: 111,699

[22] Filed: Oct. 21, 1987

[51] Int. Cl.$^4$ .............................................. A61B 5/02
[52] U.S. Cl. .................................. 128/672; 128/693; 128/713; 128/734
[58] Field of Search ............................. 128/691–694, 128/713, 734, 672, 670–671

[56] References Cited

U.S. PATENT DOCUMENTS

| Re. 30,101 | 9/1979 | Kubicek et al. . | |
|---|---|---|---|
| Re. 31,377 | 9/1983 | Mylrea et al. . | |
| 2,949,910 | 3/1957 | Brown et al. . | |
| 3,499,435 | 3/1970 | Rockwell et al. . | |
| 3,730,171 | 5/1973 | Namon . | |
| 3,734,094 | 5/1973 | Calinog . | |
| 3,742,936 | 7/1973 | Blanie et al. . | |
| 3,835,839 | 7/1974 | Brown . | |
| 3,835,840 | 9/1974 | Mount . | |
| 3,871,359 | 3/1975 | Pacela . | |
| 3,882,851 | 5/1975 | Sigworth . | |
| 3,884,219 | 5/1975 | Richardson et al. . | |
| 3,951,136 | 4/1976 | Wall . | |
| 3,994,284 | 11/1976 | Voelker . | |
| 3,996,925 | 12/1976 | Djordjevich . | |
| 4,144,878 | 3/1979 | Wheeler | 128/693 |
| 4,169,463 | 10/1979 | Piquard . | |
| 4,182,314 | 1/1980 | Boughton . | |
| 4,204,545 | 5/1980 | Yamakoshi . | |
| 4,204,548 | 5/1980 | Kurz . | |
| 4,304,239 | 12/1981 | Perlin . | |
| 4,304,240 | 12/1981 | Perlin . | |
| 4,349,031 | 9/1982 | Perlin . | |
| 4,369,794 | 1/1983 | Furler . | |
| 4,425,922 | 1/1984 | Conti et al. | 128/691 |
| 4,437,469 | 3/1984 | Djordjevich et al. | 128/693 X |
| 4,450,527 | 5/1984 | Sramek | 128/734 X |
| 4,475,555 | 10/1984 | Linder . | |
| 4,476,872 | 10/1984 | Perlin . | |
| 4,562,843 | 1/1986 | Djordjevich et al. | 128/693 X |
| 4,649,932 | 3/1987 | Smith | 128/693 X |
| 4,676,253 | 6/1987 | Newman et al. | 128/693 |

FOREIGN PATENT DOCUMENTS

81/01303 4/1982 PCT Int'l Appl. .

OTHER PUBLICATIONS

W. G. Kubicek et al., "Development and Evaluation of an Impedance Cardiac Output System," *Aerospace Medicine*, vol. 9, Dec. 1966, pp. 1208-1212.
W. G. Kubicek et al., "The Minnesota Impedance Cardiograph–Theory and Applications," *Biomedical Engineering*, Sep. 1974, pp. 410-416.

(List continued on next page.)

*Primary Examiner*—Kyle L. Howell
*Assistant Examiner*—Angela D. Sykes
*Attorney, Agent, or Firm*—Knobbe, Martens, Olson & Bear

[57] ABSTRACT

An apparatus and a method use noninvasive electrical bioimpedance measurments to monitor the mean arterial blood pressure of a patient on a continuous (heartbeat-by-heartbeat) basis. The apparatus and method process the electrical impedance across two segments of body tissue to provide a signal for each segment that indicates the increase in blood flow in each segment at the beginning of each cardiac cycle. The apparatus and method process the signals corresponding to each segment to measure the arterial pulse propagation delay between the two segments. The arterial pulse propagation delay is inversely related to the mean arterial blood pressure of the patient. The apparatus and method use the measured arterial pulse propagation delay to calculate the mean arterial blood pressure of the patient. The cardiac output of the patient is also advantageously measured and the cardiac index of the patient calculated from the cardiac output. The cardiac index and the mean arterial blood pressure are then used by the apparatus and method to calculate the left cardiac work index and the systemic vascular resistance index of the patient.

27 Claims, 2 Drawing Sheets

OTHER PUBLICATIONS

A. M. Sandman et al., "An Analogue Circuit for the Computation of Stroke Volume by the Electrical Impedance Method," *Medical and Biological Engineering,* Jan. 1976, pp. 74–78.

C. J. Bryant et al., "A Field Approach to Electrical Impedance Plethysmography," *Proceedings of the Conference on the Applications of Electronics in Medicine,* Southampton, England, Apr. 6–8, 1976, pp. 67–86.

M. Y. Jaffrin et al., "Quantitative Interpretation of Arterial Impedance Plethysmographic Signals," *Medical & Biological Engineering & Computing,* vol. 17, Jan. 1979, pp. 2–10.

K. Sakamoto et al., "Problems of Impedance Cardiography,", *Medical and Biological Engineering & Computing,* vol. 17, Nov. 1979, pp. 697–709.

H. Kunishige et al., "Simultaneous Recording of Impedance Pulse Wave on Ascending Aorta and Main Pulmonary Artery Branch (A-P Method)," *Proceedings of The Vth ICEBI,* Aug. 1981, Tokyo.

Y. Miyamoto et al., "Automatic Determination of Cardiac Output by Impedance Plethysmography Under Various Conditions," *Proceeding of the Vth ICEBI,* Aug. 1981, Tokyo.

B. Bo Sramek, "Noninvasive Technique for Measurement of Cardiac Output by Means of Electrical Impedance," *Proceedings of the Vth ICEBI,* Aug. 1981, Tokyo.

B. Bo Sramek, "Cardiac Output by Electrical Impedance," *Medical Electronics,* Apr. 1982, pp. 93–97.

B. B. Sramek et al., "Stroke Volume Equation with a Linear Base Impedance Model and Its Accuracy, As Compared to Thermodilution and Magnetic Flow Meter Techniques in Humans and Animals," *Proceedings of the VIth International Conference on Electrical Bioimpedance,* Zadar, Yugoslavia, 1983.

B. Bo Sramek, "Electrical Bioimpedance," *Medical Electronics,* Apr. 1983, pp. 95–105.

Geddes, "The Measurement of Cardiac Output and Blood Flow," Chapter Four, *Cardiovascular Devices and Their Applications,* John Wiley and Sons, New York, 1984, pp. 100–107 and 122–135.

W. Schimmler, "Physiologic und Pathophysiologic der arteriellen Pullswellengeschwindigkeit (Physiology and Pathophysiology of Arterial Pulse Velocity)," *Verh. Dtsch. Ges. Kreislaufforschg.,* 40, pp. 61–73.

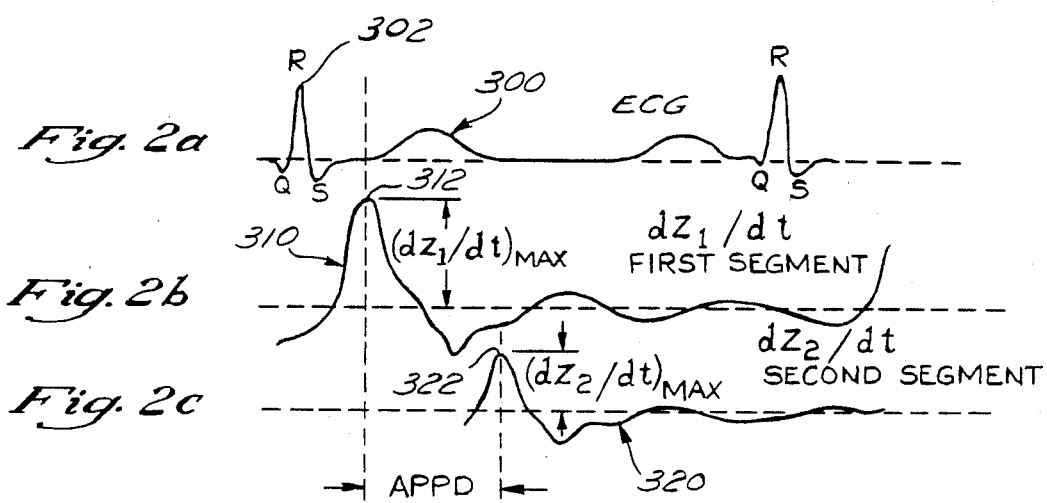
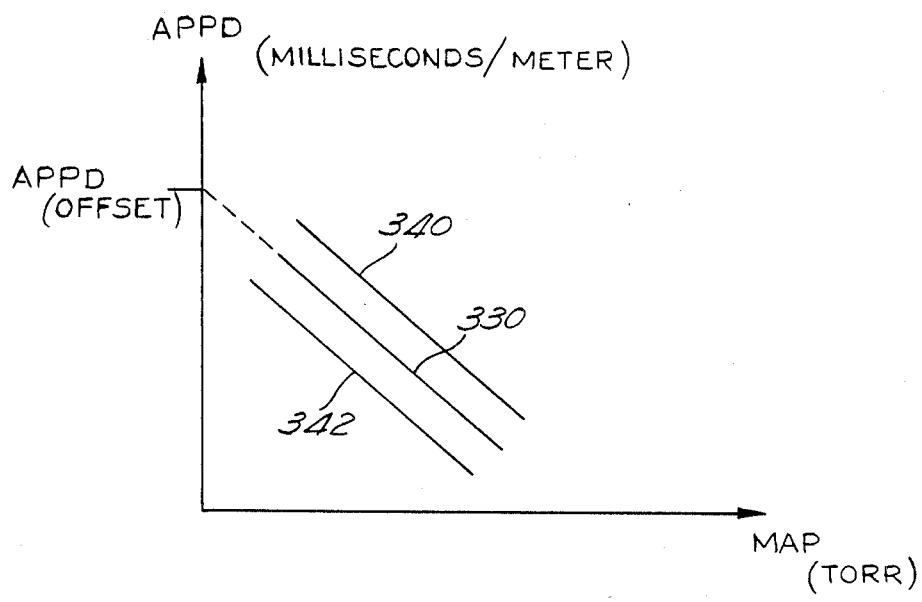

NONINVASIVE CONTINUOUS MEAN ARTERIAL BLOOD PRSSURE MONITOR

BACKGROUND OF THE INVENTION

The present invention relates to an apparatus and a method that measure mean arterial blood pressure of a patient, and, more specifically, that provide noninvasive continuous recording and analyzing of the rate of impedance changes in two sections of the patient's body in order to continuously track mean arterial blood pressure. Still more specifically, the present invention relates to a method for continuously and noninvasively measuring both mean arterial blood pressure, left cardiac work index, and systemic vascular resistance index, utilizing an apparatus capable of miniaturization.

Mean arterial blood pressure (MAP) and cardiac index (CI) together define the forces and mechanisms involved in the circulation of blood through the cardiovascular system of a body. Measurement of MAP and CI when a patient is at rest (i.e., when a patient's body is in an inactive state) determines whether a patient has normal or abnormal blood pressure and blood flow. For example, MAP values indicate whether a patient has low blood pressure (hypotensive), normal blood pressure (normotensive), or high blood pressure (hypertensive), and CI values indicate whether a patient's blood is in a low, normal, or high flow state. Measurement of MAP and CI provides invaluable clinical information for "quantifying" the extent of blood circulation abnormalities, indicating the optimal course for therapy, managing patient progress, and establishing checkpoints for rehabilitation in a patient in whom fluid status control is essential. In addition, MAP and CI measurements define other important blood circulation information and mechanisms, such as oxygen transport characteristics of the cardiovascular system. For example, multiplied by CI, multiplied by a constant (i.e., LCWI=MAP×constant) LCWI directly relates to the oxygen consumption of the pumping muscles in the heart. The systemic vascular resistance index (SVRI) is approximately equal to MAP multiplied by a constant, divided by CI (i.e., SVRI=(MAP×constant)/CI SVRI is inversely proportional to the global oxygen demand of a body, and also represents a major component of the afterload on the heart.

For many diagnostic purposes, a resting measurement of MAP is important for determining the condition of a patient's cardiovascular system. A normal cardiovascular system is characterized by sufficient flow of blood to all parts of a patient's body, especially the brain and cardiac muscle, without producing prolonged strain on the physical capabilities of various organs through which blood flows.

In an abnormal cardiovascular system, blood pressure may be too high or too low, with each abnormality having attendant consequences for various body parts. Prolonged high blood pressure (hypertension) strains various organs in a patient's body and may end in heart failure, a cerebrovascular accident (stroke), or kidney damage. Knowledge that a patient is hypertensive informs a clinician to administer certain drugs and place the patient on a specified diet (e.g., one with a reduced sodium intake) to control the condition. Also, it can aid a clinician in discovering tumors or diseases that have afflicted a patient and that have caused the hypertension. Prolonged low blood pressure (hypotension) is typical when a patient has undergone hemorrhaging, through an accident or surgery. Hypotension can reduce the flow of blood to all parts of a patient's body, most seriously the brain and cardiac muscle, causing irreparable damage to those parts. Knowledge that a patient is hypotensive informs a clinician to use methods to raise the blood pressure of the patient.

Because blood is electrically the most conductive substance within any body segment, electrical bioimpedance measurements permit quantification of blood flow as a result of changes in electrical conductivity in a body segment. For example, the electrical impedance technique used for measuring cardiac output is based on changes in thoracic electrical impedance caused by cardiovascular activity. The impedance changes are measured by causing the flow of a fixed frequency constant magnitude current across a segment of a patient's body and sensing a voltage that is directly proportional to the instantaneous impedance. A number of devices have been developed to measure the impedance changes in body tissue resulting from blood flow, and correspondingly can accurately measure cardiac output (CO). However, none of these devices use bioimpedance techniques to measure blood pressure.

Thus, there is a need for a device that can accurately and continuously measure MAP through bioimpedance techniques so that one homogeneous technology can be used to measure and calculate MAP, LCWI, SVRI, and CI. The device can be miniaturized using microelectronic circuitry.

The need for such a bioimpedance device is evident from the fact that current methods for measuring arterial blood pressure are all based on the sphygmomanometric principle. In a typical sphygmomanometric measurement, an inflatable cuff is wrapped about a patient's upper arm and inflated so that it presses in on the arm. A determination of the systolic and diastolic pressure of a cardiovascular system is then made manually or automatically by monitoring the heartbeat of the patient as the pressure in the cuff decreases over time. In combination with an oscilloscope, the sphygmomanometric technique can measure MAP, but typically MAP is estimated from systolic and diastolic pressure by the following formula:

$$MAP = \frac{P_{systolic} - P_{diastolic}}{3} + P_{diastolic} \quad (1)$$

where $P_{systolic}$ is the systolic blood pressure and $P_{diastolic}$ is the diastolic blood pressure. Thus, current methods for measuring MAP provide mere estimates, which may not be accurate enough for a clinician to properly diagnose problems in a patient's body.

From a practical point of view, use of sphygmomanometry involves four additional drawbacks. First, it determines the average blood pressure over a plurality of heartbeats, and thus is in reality a series of tests. In addition, because systolic pressure is measured first, followed by a diastolic pressure measurement after a passage of time, the measurements are unlikely to correlate to the actual respective pressures at a given time. For example, the diastolic pressure may be different at the time the systolic pressure is measured, or the systolic pressure may be different by the time the diastolic pressure is measured because of the time delay between the two measurements. Second, the inflatable cuff hinders the flow of blood through the extremity to which it is attached (i.e., a patient's arm), and thus reduces the flow of blood to the portion of the extremity on the side of the cuff opposite from the heart. An adverse result of this reduction in blood flow is that ulnar nerve injury might occur if the measurement of blood pressure is repeated too frequently. Third, automated equipment for measurement of blood pressure requires pneumatic pumps and control valves that are bulky and have high power demand. Fourth, because of its size while inflated, the cuff limits the physical activity of a patient while a measurement is being taken. Also, if the cuff is connected to a device that automatically measures blood pressure, a patient's activity is further limited because the cuff is connected to bulky, possibly stationary pneumatic pumps and control valves.

Thus, there is a need for a device that can accurately and continuously measure MAP without hindering blood flow to any part of a patient's body or limiting the physical activity of a patient while MAP is being measured.

SUMMARY OF THE INVENTION

The present invention overcomes the deficiencies of prior art devices by providing an apparatus and a method for continuously and noninvasively measuring and monitoring mean arterial blood pressure (MAP), left cardiac work index (LCWI), and systemic vascular resistance (SVRI) through the use of electrical bioimpedance techniques that do not hinder blood flow or limit the physical activity of a patient, and by providing an apparatus that can be miniaturized.

The present invention includes a noninvasive apparatus for continuously monitoring the mean arterial blood pressure of a patient. The apparatus comprises a first electrical bioimpedance measuring device that is electrically connectable to a first segment of the patient's body (for example, on the thorax) to sense the increase in blood flow in the first segment caused by the ejection of blood into the arteries during the ventricular contraction of the patient's heart and to generate a first output signal that indicates when the increase in blood flow occurs in the first segment. The apparatus further includes a second electrical bioimpedance measuring device that is electrically connectable to a second segment of the patient's body to sense the increase in blood flow in the second segment caused by the ejection of blood into the arteries during the ventricular contraction of the patient's heart and to generate a second output signal that indicates when the increase in blood flow occurs in the second segment. The second segment located at a distance from the first segment (for example, on the calf) so that the increase in blood flow in the second segment occurs at a time interval after the increase in blood flow in the first segment. The time interval between the first output signal and said second output signal is proportional to the distance between the first segment and the second segment and inversely related to the mean arterial blood pressure of the patient. The apparatus also includes an electronic measuring and calculating circuit that measures the time interval between the first output signal and the second output signal, and that calculates the mean arterial blood pressure of the patient based upon the measured time interval and the distance between the first segment and the second segment.

In preferred embodiments of the apparatus, the first electrical bioimpedance measuring device comprises a current source having a high-frequency constant amplitude electrical current output; first and second injector electrodes positionable on the patient to inject the output of the current source into the first segment of the patient (e.g., in the thorax); and first and second sensor electrodes positionable on the patient proximate to the first and second injector electrodes to sense a voltage caused by current flow through the first segment of the patient. The sensed voltage has a magnitude that varies in accordance with changes in electrical bioimpedance of the first body segment caused by the flow of blood in the first body segment during each cardiac cycle. Such preferred embodiments further include an electronic circuit connected to the first and second sensor electrodes to receive the voltage sensed by the sensor electrodes and to generate a first output signal having a magnitude that changes in accordance with the blood flow in the first segment during each cardiac cycle. In such embodiments, the electronic circuit preferably includes a differentiator that generates a differentiated voltage that has a magnitude proportional to the rate of change of electrical bioimpedance in the first segment. The differentiated voltage has at least one peak corresponding to the maximum rate of increase in blood flow in the first segment caused by the ventricular contraction of the patient's heart.

In like manner, the second electrical bioimpedance measuring device preferably comprises a current source having a high-frequency constant amplitude electrical current output; third and fourth injector electrodes positionable on the patient to inject the output of said current source into the second segment of the patient (e.g., in the calf); third and fourth sensor electrodes positionable on said patient proximate to said third and fourth injector electrodes to sense a voltage caused by current flow through the second segment of the patient. The sensed voltage has a magnitude that varies in accordance with changes in electrical bioimpedance of the second body segment caused by the flow of blood in the second body segment during each cardiac cycle. The preferred embodiment of the second electrical bioimpedance device further includes an electronic circuit connected to the third and fourth sensor electrodes to receive the voltage sensed by the third and fourth sensor electrodes and to generate a second output signal having a magnitude that changes in accordance with the blood flow in the second body segment during each cardiac cycle. In such embodiments, the electronic circuit preferably includes a differentiator that generates a differentiated voltage that has a magnitude proportional to the rate of change of electrical bioimpedance in the second segment. The differentiated voltage has at least one peak corresponding to the maximum rate of increase in blood flow in the second segment caused by the ventricular contraction of the patient's heart.

Preferably, the electronic measuring and calculating circuit is a microprocessor that is responsive to said first output signal from the first electrical bioimpedance measuring device and to the second output signal from the second electrical bioimpedance measuring device. The microprocessor measures the time interval between the increase in blood flow indicated by the first output signal and the increase in blood flow indicated by the second output signal.

The apparatus preferably includes an input device electrically connected to the microprocessor. The input device is operable to provide data input to the microprocessor that represents the distance between the first and second segments.

The electronic measuring and computing circuit preferably generates an output signal that represents the mean arterial blood pressure of the patient. Also preferably, it includes a display device electrically connected to said electronic measuring and computing circuit that displays the mean arterial blood pressure of the patient.

In particularly preferred embodiments of the apparatus, the electronic measuring and computing circuit includes a means for generating a time window that begins at a predetermined time after the increase in blood flow indicated by the first output signal and that has a predetermined duration. The electronic measuring and computing circuit monitors the second output signal only during the time window thereby reducing the probability of incorrect measurement of the time interval between the beginning of blood flow in the first segment and the beginning of blood flow in the second segment. The time window can be advantageously implemented in software or hardware.

The electronic measuring and computing circuit preferably calculates the mean arterial blood pressure of the patient in accordance with the following relationship:

$$MAP = \frac{\left(\frac{APPD}{D} - APPD_{offset}\right)}{SLOPE}$$

where MAP is the calculated mean arterial blood pressure, D is the vascular distance between the two body segments, APPD is the measured arterial pulse propagation delay, $APPD_{offset}$ is an empirically determined offset in the measure delay, and SLOPE is an empirically determined relationship between the change in the measured delay and the change in the mean arterial blood pressure. For example, for an exemplary patient, SLOPE is approximately $-0.875$ milliseconds per meter per torr and $APPD_{offset}$ is approximately 210 milliseconds.

In particularly preferred embodiments, the first electrical bioimpedance measuring device provides an output signal having a magnitude corresponding to the measured cardiac output of the patient. The electronic measuring and computing circuit converts the measured cardiac output to a magnitude corresponding to the cardiac index of the patient. The electronic measuring and computing circuit then calculates the left cardiac work index of the patient in accordance with the following relationship:

LCWI=MAP×CI×CONSTANT where LCWI is the left cardiac work index of the patient, MAP is the mean arterial blood pressure of the patient, CI is the cardiac index of the patient, and CONSTANT is a constant selected for the parameters of the cardiac index and the pressure. The electronic measuring and computing circuit also advantageously calculates the systemic vascular resistance index of the patient in accordance with the following relationship:

SVRI=(MAP/CI)×CONSTANT where SVRI is the systemic vascular resistance index of the patient, MAP is the mean arterial blood pressure of the patient, CI is the cardiac index of the patient, and CONSTANT is a constant selected for the parameters of the cardiac index and the pressure.

The electrical bioimpedance measuring devices for sensing the blood flow in the segments are advantageously devices similar to that described in U.S. Pat. No. 4,450,527 for a NONINVASIVE CONTINUOUS CARDIAC OUTPUT MONITOR, assigned to the assignee of the present application. U.S. Pat. No. 4,450,527 is incorporated herein by reference. Other commercially available electrical bioimpedance measuring devices can also be used. The device disclosed in U.S. Pat. No. 4,450,527 detects changes in the electrical bioimpedance of a body segment with respect to time (i.e., dZ/dt) caused by the flow of blood in the body segment resulting from the pumping action of the heart. Thus, the changes in the electrical bioimpedance are synchronized with the pumping action of the heart. The time at which the changes in electrical bioimpedance occur with respect to the beginning of a cardiac cycle is determined by the distance of the body segment from the heart and the rate at which the blood flows in the arteries interconnecting the body segment with the heart. The blood flow rate is in turn a function of the mean arterial blood pressure. The present invention measures the amount of time (i.e., the propagation delay) between the occurrence of electrical bioimpedance changes at the first segment of the body (e.g., at the thoracic segment) and the occurrence of corresponding changes in the second body segment (e.g., the lower calf) of the patient. The propagation delay between the corresponding changes in the two body segments is used by the electronic measuring and calculating circuit to compute the mean arterial blood pressure (MAP) of the patient.

As set forth above, in preferred embodiments of the present invention, the electrical bioimpedance measuring device electrically connected to the thoracic electrodes calculates the cardiac output (CO) from the measured electrical bioimpedance changes and provides the cardiac output (CO) as an output. One such device that provides the cardiac output as an output is the NCCOM® noninvasive continuous cardiac output monitor, commercially available from BioMed Medical Manufacturing Ltd., 5 Wrigley Street, Irvine, Calif. 92718, that uses bioimpedance measuring techniques to measure blood flow parameters, such as the cardiac index. The operation of such a unit is described in U.S. Pat. No. 4,450,527 and in the product literature available from BoMed Medical Manufacturing Ltd. The cardiac index (CI) of a patient is the cardiac output (CO) of the patient normalized to the patient's body weight or to the surface area of the patient. The cardiac output of the patient is provided as an additional input to the computing means along with the patient's weight or surface area. In addition to calculating MAP, the computing means utilizes the cardiac output (CO) to calculate LCWI, and SVRI.

In preferred embodiments of the present invention, the apparatus is miniaturized using microelectronics to provide portability so that the blood pressure of a patient can be continuously monitored without totally impairing the patient's mobility.

The present invention further includes a method for noninvasively monitoring the mean arterial blood pressure of a patient. The method comprises the steps of electrically connecting a first electrical bioimpedance measuring device to a first segment of the patient' body, sensing the increase in blood flow in the first segment caused by the ejection of blood into the arteries during the ventricular contraction of the patient's heart, and generating a first output signal that indicates when the increase in blood flow occurs in the first segment. The method further includes the steps of electrically connecting a second electrical bioimpedance measuring device to a second segment of the patient's body, sensing the increase in blood flow in the second segment caused by the ejection of blood into the arteries during the ventricular contraction of the patient's heart, and generating a second output signal that indicates when the increase in blood flow occurs in the second segment. The method includes the step of locating the second segment at a distance from the first segment so that the increase in blood flow in the second segment occurs at a time interval after the increase in blood flow in the first segment, the time interval between the first output signal and the second output signal proportional to the distance between the first segment and the second segment and inversely proportional to the mean arterial blood pressure of the patient. The method also includes the steps of measuring the time interval between the first output signal and the second output signal, and calculating the mean arterial blood pressure of the patient based upon the measured time interval and the distance between the first segment and the second segment.

In preferred embodiments of the invention, the step of sensing the blood flow in the first segment comprises the steps of generating a high-frequency constant amplitude electrical current, injecting the current into the first segment of the patient, sensing a voltage caused by current flow through the first segment of the patient, the voltage having a magnitude that varies in accordance with changes in electrical bioimpedance of the first segment caused by the flow of blood in the first segment during each cardiac cycle, and amplifying the sensed voltage and generating a first output signal having a magnitude that changes in accordance with the blood flow in the first segment during each cardiac cycle.

Preferably, the method further includes the step of generating a differentiated voltage that has a magnitude proportional to the rate of change of electrical bioimpedance in the first segment. The differentiated voltage has at least one peak corresponding to the maximum rate of increase in blood flow in the first segment caused by the ventricular contraction of the patient's heart.

Also preferably, the step of sensing the blood flow in the second segment comprises the steps of generating a high-frequency constant amplitude electrical current, injecting the current into the second segment of the patient; sensing a voltage caused by current flow through the second segment of the patient, the voltage having a magnitude that varies in accordance with changes in electrical bioimpedance of the second segment caused by the flow of blood in the second segment during each cardiac cycle; and amplifying the sensed voltage and generating a second output signal having a magnitude that changes in accordance with the blood flow in the first segment during each cardiac cycle. The method also preferably includes the step of generating a differentiated voltage that has a magnitude proportional to the rate of change of electrical bioimpedance in the first segment, the differentiated voltage having at least one peak corresponding to the maximum rate of increase in blood flow in the second segment caused by the ventricular contraction of the patient's heart.

In preferred embodiments, the calculating step is performed by a microprocessor, and the method further includes the step of inputting data to the microprocessor representative of the distance between the first and second segments.

Preferably, the method generates an output signal that represents the mean arterial blood pressure of the patient. Also preferably, the method displays the mean arterial blood pressure of the patient.

Alternative embodiments of the method include the step of generating a time window that begins at a predetermined time after the increase in blood flow indicated by the first output signal and that has a predetermined duration. The measuring step is operational to measure the end of the time interval only during the time window to thereby reduce the probability of incorrect measurement of the time interval between the beginning of blood flow in the first segment and the beginning of blood flow in the second segment.

Preferably, the calculating step is performed in accordance with the following relationship:

$$MAP = \frac{\left(\frac{APPD}{D} - APPD_{offset}\right)}{SLOPE}$$

where MAP is the calculated mean arterial blood pressure, D is the vascular distance between the two segments, APPD is the measured arterial pulse propagation delay, $APPD_{offset}$ is an empirically determined offset in the measure delay, and SLOPE is an empirically determined relationship between the change in the measured delay and the change in the mean arterial blood pressure. In exemplary embodiments of the method, SLOPE is approximately $-0.875$ milliseconds per meter per torr and $APPD_{offset}$ is approximately 210 milliseconds.

The method advantageously further includes the steps of providing an output signal having a magnitude corresponding to the measured cardiac output of the patient; converting the measured cardiac output to a magnitude corresponding to the cardiac index of the patient; and calculating the left cardiac work index of the patient in accordance with the following relationship:

LCWI=MAP×CI×CONSTANT where LCWI is the left cardiac work index of the patient, MAP is the mean arterial blood pressure of the patient, CI is the cardiac index of the patient, and CONSTANT is a constant selected for the parameters of the cardiac index and the pressure.

The method advantageously further includes the steps of providing an output signal having a magnitude corresponding to the measured cardiac output of the patient; converting the measured cardiac output to a magnitude corresponding to the cardiac index of the patient; and calculating the systemic vascular resistance index of the patient in accordance with the following relationship:

SVRI=(MAP/CI)×CONSTANT where SVRI is the systemic vascular resistance index of the patient, MAP is the mean arterial blood pressure of the patient, CI is the cardiac index of the patient, and CONSTANT is a constant selected for the parameters of the cardiac index and the pressure.

BRIEF DESCRIPTION OF THE DRAWINGS

FIGS. 2a, 2b, and 2c are graphs of the timing relationship between the electrical activity of the heart, the rate of change of segmental impedance (dZ/dt) as a function of time in the first segment, and the rate of change of segmental impedance (dZ/dt) as a function of time in the second segment, respectively, during one heartbeat.

FIG. 3 is a graph of the relationship between normalized APPD and MAP.

DETAILED DESCRIPTION OF THE PREFERRED EMBODIMENT OF THE APPARATUS

Figure 1:
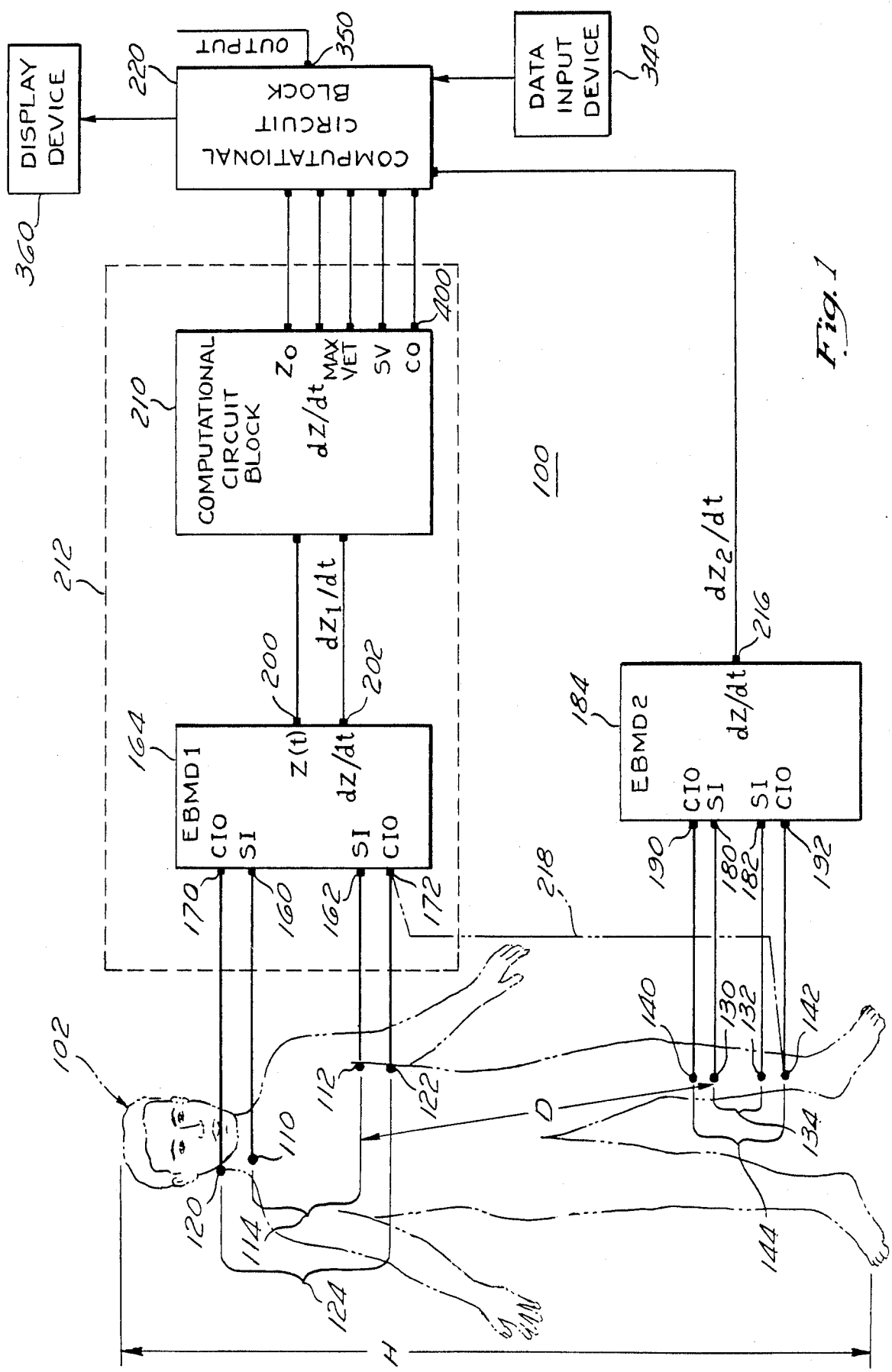
FIG. 1 is a block diagram that illustrates the apparatus interconnected with a patient, showing a first body segment on the patient's thorax and a second body segment on the patient's calf.

FIG. 1 illustrates the use of an especially preferred embodiment of an apparatus 100 constructed in accordance with the present invention showing the interconnections to a patient 102 to perform the steps of a typical MAP measuring and monitoring test in accordance with the method of the present invention. A first voltage sensing electrode 110 is shown attached to the neck area of the patient 102 at the intersection of the line encircling the root of the neck and the right frontal plane. A second voltage sensing electrode 112 is attached on the patient's left side on the left mid-axillary line at the xiphoid process level. The first voltage sensing electrode 110 and the second voltage sensing electrode 112 delineate a first inner body segment 114 that includes the tissues and fluids of the thorax between the two electrodes. A first current injecting electrode 120 is attached to the patient's neck approximately five centimeters above the first sensing electrode 110. A second current injecting electrode 122 is attached to the patient approximately five centimeters below the second sensing electrode 112 along the mid-axillary line. The first current injecting electrode 120 and the second current injecting electrode 122 delineate a first outer body segment 124 that includes the tissues and fluids of the thorax between the two electrodes. The first inner body segment 114 is included within the first outer segment 124.

A third voltage sensing electrode 130 is attached to the upper part of a patient's calf. A fourth voltage sensing electrode 132 is attached to the lower part of a patient's calf. The third voltage sensing electrode 130 and the fourth voltage sensing electrode 132 delineate a second inner body segment 134 that includes the tissues and fluids of the patient's calf between the two electrodes. A third current injecting electrode 140 is attached to the patient approximately five centimeters above the third voltage sensing electrode 130. A fourth current injecting electrode 142 is attached to the patient approximately five centimeters below the fourth voltage sensing electrode 132. The third current injecting electrode 140 and the fourth current injecting electrode 142 delineate a second outer body segment 144 that includes the tissues and fluids of the patient's calf between the two electrodes. The second inner body segment 134 is included within the second outer body segment 144.

The electrodes 110, 112, 120, 122, 130, 132, 140, and 142 are advantageously standard spot, pre-gelled disposable ECG electrodes or other readily available electrodes. Although other electrodes, such as band electrodes, can be used, the spot electrodes are particularly advantageous because they are inexpensive, disposable and relatively comfortable to wear during exercise or long-term monitoring.

It should be understood that although single electrodes are shown, in many applications each of the single electrodes can be advantageously connected to a second electrically connected electrode. For example, in FIG. 1, the first current injecting electrode 120 is shown on the lefthand side of the neck of the patient 102. An additional current injecting electrode (not shown) can be electrically connected to the first current injecting electrode 120 and positioned on the corresponding location on the righthand side of the neck. Similar electrodes can be electrically connected to the second current injecting electrode 122, the first current sensing electrode 110 and the second current sensing electrode 112, respectively. In such an application, each pair of electrically interconnected electrodes are symmetrically disposed about the frontal centerline of the patient 102.

The first voltage sensing electrode 110 and the second voltage sensing electrode 112 are electrically connected to a first voltage sensing input 160 and a second voltage sensing input 162 of a first electrical bioimpedance measuring device (EBMD1) 164. The first current injecting electrode 120 and the second current injecting electrode 122 are electrically connected to a first current injecting output 170 and a second current injecting output 172, respectively, of the first electrical bioimpedance measuring device 164. In like manner, the third voltage sensing electrode 130 and the fourth voltage sensing electrode 132 are electrically connected to a first voltage sensing input 180 and a second voltage sensing input 182 of a second electrical bioimpedance measuring device (EBMD2) 184. The third current injecting electrode 140 and the fourth current injecting electrode 142 are electrically connected to a first current injecting output 190 and a second current injecting output 192, respectively, of the second electrical bioimpedance measuring device 184.

The first electrical bioimpedance measuring device 164 is advantageously a commercially available device such as the NCCOM ® noninvasive continuous cardiac output monitor commercially available from BoMed Medical Manufacturing Ltd., 5 Wrigley Street, Irvine, Calif. 92718. The operation of the electrical bioimpedance measuring device 164 is described in U.S. Pat. No. 4,450,527, incorporated herein by reference. The operation of an exemplary bioimpedance measuring device is also disclosed by B. Sramek in "ELECTRICAL BIOIMPEDANCE," *MEDICAL ELECTRONICS*, April 1983, pp. 95-105, also incorporated herein by reference.

Briefly, the first electrical bioimpedance measuring device 164 generates a high frequency, constant current that is injected into the patient's body so that it flows through the first outer segment 124 between the first current injecting electrode 120 and the second current injecting electrode 122. The current flowing through the tissues and fluids of the first outer segment 124 also necessarily flows through the first inner segment 114. The flow of current through the electrical impedance of the tissues and the fluids of the first inner segment 114 generates a voltage that is sensed by the first sensing electrode 110 and the second sensing electrode 112 and that is provided as an input to the first electrical bioimpedance measuring device 164 between the first voltage sensing input 160 and the second voltage sensing input 162. The changes in electrical bioimpedance of the first inner segment 114 caused by changes in the quantity of fluid in the first inner segment 114 cause the magnitude of the voltage sensed between the first sensing electrode 110 and the second voltage sensing electrode 112.

The first electrical bioimpedance measuring device 164 receives the sensed voltage from the first voltage sensing electrode 110 and the second voltage sensing electrode 112, amplifies the sensed voltage, and filters out the high frequency components to provide a time-varying voltage $Z(t)$ that has a magnitude that varies in accordance with the changes in electrical bioimpedance of the first inner body segment 114. (The designation $Z(t)$ is used herein to indicate that the time-varying voltage represents the electrical bioimpedance of the inner body segment 114.) This time-varying voltage $Z(t)$ is provided as a $Z(t)$ output voltage on a first $Z(t)$ output terminal 200. The first electrical bioimpedance measuring device 164 differentiates the time-varying voltage $Z(t)$ to provide a first differentiated output voltage $dZ_1/dt$ on a first $dZ/dt$ output terminal 202 that has a magnitude proportional to the rate of change of the electrical bioimpedance of the first inner body segment 114. (Again, the designation $dZ/dt$ is used to indicate that the differentiated output voltage represents the rate of change of the electrical bioimpedance.) The time-varying voltage $Z(t)$ and the first differentiated voltage $dZ_1/dt$ are provided as inputs to computational circuitry represented by a first computational circuit block 210 that processes the $Z(t)$ and $dZ_1/dt$ voltage waveforms and generates quantitative information regarding the patient's cardiovascular system. The computational circuitry represented by the first computational circuit block 210 is advantageously included as part of the first electrical bioimpedance measuring device 164. Thus, the first electrical bioimpedance measuring device 164 and the first computational circuit block 210 are show as part of an overall block 212 (in dashed lines). For example, the block 212 can advantageously represent the NCCOM ® noninvasive continuous cardiac output monitor available from BoMed Medical Manufacturing Ltd. which calculates the base impedance $Z_0$ of the first inner body segment 114, the ventricular ejection time (VET) of the heart, the maximum rate of impedance change, the stroke volume (SV) of the heart, the heart rate and the cardiac output (CO).

The second electrical bioimpedance measuring device 184 can also advantageously be an NCCOM ® noninvasive continuous cardiac output monitor available from BoMed Medical Manufacturing Ltd. In the alternative, the second electrical bioimpedance measuring device 184 can be a simpler electrical bioimpedance measuring device, such as the BIOCON ™ electrical bioimpedance converter also available from BoMed Medical Manufacturing Ltd., which operates in a manner similar to that described above for the NCCOM ® noninvasive continuous cardiac output monitor. The second electrical bioimpedance measuring device generates a high frequency, constant current that is injected into the second outer body segment 144 between the third current injecting electrode 130 and the fourth current injecting electrode 132. The current flowing through the tissues and fluids of the second inner body segment generates a voltage that is sensed by the third voltage sensing electrode 140 and the fourth voltage sensing electrode 142. The sensed voltage is provided as an input to the second electrical bioimpedance measuring device 184 between the first voltage sensing input terminal 180 and the second voltage sensing input terminal 182 of the second electrical bioimpedance measuring device 184. The second electrical bioimpedance measuring device 164 amplifies, filters and differentiates the sensed voltage to provide a second differentiated output voltage $dZ_2/dt$ on a $dZ/dt$ output terminal 216. Unlike the NCCOM ® noninvasive continuous cardiac output monitor, described above, the BIOCON ™ electrical bioimpedance converter does not include any computational circuitry and provides only a $dZ/dt$ output signal ($dZ_2/dt$) on an output terminal 216 that represents the rate of change of electrical bioimpedance of the second inner body segment 134.

In an alternative embodiment, a common constant current source is advantageously used for the two electrical bioimpedance measuring devices. In such an embodiment, the common constant current source is electrically connected to the first current injecting electrode 120 on the neck of the patient 102 and to the fourth current injecting electrode 142 on the lower portion of the patient's calf. This electrical interconnection is illustrated by a phantom line 218 from the second current injecting output 172 of the second electrical bioimpedance measuring device 164 to the fourth current injecting electrode 142. It should be understood that in the alternative embodiment, the second current injecting electrode 122 and the third current injecting electrode 130 are not used. Furthermore, in the alternative embodiment, the second electrical bioimpedance measuring device 184 does not include a current source and there is no connection from the second electrical bioimpedance measuring device 184 to either the third current injecting electrode 130 or the fourth current injecting electrode 142. In this alternative embodiment, the constant current generated by the first electrical bioimpedance measuring device 164 flows between the first current injecting electrode 120 and the fourth current injecting electrode 142 and thus flows through the thorax and the calf of the patient 102. The voltage generated by the constant current flowing in the thorax is sensed by the first voltage sensing electrode 110 and the second voltage sensing electrode 112, and the voltage generated by the same constant current flowing in the calf is sensed by the third voltage sensing electrode 130 and the fourth voltage sensing electrode 132, as before. This particular embodiment is particularly advantageous with respect to the miniaturization of the electronics since only one constant current generator is needed, thus reducing the total electronic circuitry required.

The first differentiated output signal $dZ_1/dt$ from the terminal 202 of the first electrical bioimpedance device 164 and the second differentiated output signal $dZ_2/dt$ from the terminal 216 of the second electrical bioimpedance measuring device 184 are provided as inputs to a second computational circuit block 220. The second computational circuit block 220 includes conventional peak detection circuits (not shown) that detect the peak magnitudes of the two differentiated output voltages. The second computational circuit block 220 further includes a digital timer, a software timing loop, or the like, (not shown) that measures the time delay between the two peaks. The second computational circuit block 220 calculates the mean arterial blood pressure (MAP)

of the patient 102 based upon the measured time delay between the two peaks. The measurement of the time delay and the calculation of the mean arterial blood pressure are advantageously performed during each cardiac cycle so that the mean arterial blood pressure is monitored continuously.

The theory upon which the computation of the mean arterial blood pressure is based is described below.

DESCRIPTION OF THE METHOD OF CALCULATING MAP

As is well known in the art, the differentiated output voltages produced an electrical bioimpedance measuring device, such as the first electrical bioimpedance measuring device 164, includes a peak magnitude once each cardiac cycle that is caused by the rapid infusion of blood into the first inner body segment 114 and the resulting decrease in the electrical bioimpedance of the first inner body segment 114. The infusion of blood is caused by the pumping action of the patient's heart during the systolic portion of the cardiac cycle. The time at which the peak magnitude occurs depends in part upon the location of the first inner body segment 114 with respect to the heart. For example, FIGS. 2a and 2b illustrate the time relationship between the beginning of the cardiac cycle and peak magnitude of the differentiated electrical bioimpedance signal of the first inner body segment 114.

FIG. 2a is a graph of an exemplary electrocardiograph (ECG) waveform 300 that represents the electrical activity of the patient's heart. The ECG waveform 300 includes a peak 302 at the beginning of the cardiac cycle typically referred to as the QRS complex of the ECG. The R portion of the QRS complex is caused by the ventricular depolarization at the beginning of the ventricular contraction of the heart. FIG. 2b is a simplified graph 310 of the differentiated voltage dZ/dt produced by the first electrical bioimpedance measuring device 164. The dZ/dt graph 310 includes a peak 312 that represents the maximum rate of change (i.e., $(dZ_1/dt)_{max}$) in the electrical bioimpedance caused by the infusion of blood into the tissues of the first inner body segment 114. This maximum rate of change corresponds to the peak ejection velocity (PEV) of the blood from the left ventricle of the heart. As illustrated, the dZ/dt peak 312 is delayed in time from the ECG peak 302 by an amount of time referred to as the pre-ejection period (PEP) of the heart. This is the time required for the left ventricle of the heart to fully contract and eject the blood into the aorta where the increase in the blood perfusion of the thorax of the patient causes the decrease in electrical bioimpedance and thus the dZ/dt peak 312 in the dZ/dt waveform 310.

In like manner, FIG. 2c is a graph of a voltage waveform 320 that represents the second differentiated voltage output $dZ_2/dt$ of the second electrical bioimpedance measuring device 184. The voltage waveform 320 has a peak 322 representing $(dZ_2/dt)_{max}$ that is caused by the rapid decrease in electrical bioimpedance of the second inner body segment 134 that results from the flow of blood in the patient's calf. As illustrated the peak 322 of the voltage waveform 320 is displaced in time from the peak 312 of the voltage waveform 310 of FIG. 2b and is thus delayed further in time from the R wave 302 of the QRS complex in the ECG waveform 300.

The time delay between the peak 312 of the voltage waveform 310 (FIG. 2b) representing the first differentiated output voltage $dZ_1/dt$ (i.e., the voltage corresponding to the changes in electrical bioimpedance in the first inner body segment 114 of the thorax) and the peak 322 of the voltage waveform 320 (FIG. 2c) representing the second differentiated output voltage $dZ_2/dt$ (i.e., the voltage corresponding to the changes in electrical bioimpedance in the second inner body segment 134 of the calf) corresponds to the time interval during which the blood ejected from the heart at the peak velocity travels from the first inner body segment 114 of the thorax to the second inner body segment 134 of the calf. This time interval is referred to as the arterial pulse propagation delay (APPD).

The APPD depends in part upon the vascular distance from the first inner body segment 114 to the second inner body segment 134 and in part upon the propagation velocity of the blood flowing from the aorta in the thorax to the arteries in the calf of the patient. Since the distance remains constant for a given patient once the electrodes defining the two inner body segments have been applied, the APPD is primarily a function of the propagation velocity of the blood. The propagation velocity of the blood, referred to as the arterial pulse propagation velocity (APPV), is in turn dependent upon the mean arterial blood pressure (MAP). It has been found that the relationship between the propagation velocity of the blood with respect to the mean arterial blood pressure is such that the APPD has an almost linear relationship to the mean arterial blood pressure over the expected range of blood pressures for a patient. See, for example, W. Schimmler, "Physiologic und Pathophysiologic der arteriellen Pulswellengeschwindigkeit [Physiology and Pathophysiology of Arterial Pulse Velocity]," *Verh. Dtsch. Ges. Kreislaufforscho.*, 40, pp. 61–73, wherein the arterial pressure pulse propagation velocity (c) is defined as a function of arterial module of elasticity (E), the thickness of the arterial wall (h), radius (r) of the artery, and blood density (D) as follows:

$$c = \sqrt{\frac{E \times h}{2r \times D}} \quad (2)$$

Schimmler's formula, represented by Equation (2), was originally used to measure flexibility of the arteries. However, the present invention uses the relationship as a basis for a new method of determining mean arterial pressure.

The arterial pressure pulse propagation velocity (APPV) is related to the arterial pulse propagation delay (APPD) by the distance over which the delay is measured because the velocity equals the distance travelled multiplied by the time taken to travel that distance. The mean arterial blood pressure affects E, r, and D in Schimmler's formula in such a way that there is a well defined, almost linear inverse relationship between APPD and MAP that is used to calculate the mean arterial blood pressure (MAP). For APPD to be linearly related to MAP, APPD must first be normalized to account for differences in the heights of patients. Normalization is required because the distance traveled from the first segment to the second segment will be farther for a taller patient and less for a shorter patient. Thus, APPD depends directly on a patient's height. Generally, human adults are anatomically proportional, and APPD can be normalized so that it is independent of height. The proportionality in adult anatomy means that the distance traveled from the first inner segment 114 of the thorax to the second inner segment 134 of the calf is the same in terms of the percentage of a patient's overall height. For example, if two patients have heights H1 and H2, the distance between the first inner body segments 114 of their respective thoraxes and the second inner body segments 134 of their respective calves would be an approximately equal fraction of their heights, assuming consistent placements of the electrodes that define the body segments. For example, for the exemplary placements of the electrodes set forth above in connection with FIG. 1, the vascular distance between the first inner body segment 114 of the thorax and the second inner body segment of the calf of a patient is approximately 55% of the height of a typical patient. In other words the vascular distance between the two segments of a patient having an overall height H1 will be 0.55×H1, and the vascular distance between the two segments of a patient having a height H2 will be 0.55×H2. Thus, the measured APPD in each patient can be divided by the patient's height to calculate a normalized APPD so that the patient's height is no longer a factor.

The inverse linear relationship between the normalized arterial pulse propagation delay (APPD) (i.e., measured APPD divided by the normalization factor 0.55×H in the present example) and the mean arterial blood pressure (MAP) for an exemplary patient is illustrated by a curve 330 on a graph in FIG. 3 for the normal MAP range of 60-150 torrs (mm Hg). As illustrated, an increase in mean arterial blood pressure (to the right along the horizontal axis of the graph in FIG. 3) results in a decrease in the APPD (downward along the vertical axis in FIG. 3).

From the graph in FIG. 3, it can be seen that for an exemplary patient, the following relationship exists between the measured arterial pulse propagation time (APPD), the vascular distance (D) between the two body segments, and the mean arterial blood pressure (MAP):

$$APPD = D \times ((SLOPE \times MAP) + APPD_{offset}) \quad (3)$$

where APPD is the arterial pulse propagation delay in milliseconds, D is the vascular distance in meters, SLOPE is the slope of the graph in FIG. 3 in milliseconds per torr per meter, MAP is the mean arterial blood pressure in torr, and $APPD_{offset}$ is the intersection of the extension of the graph 330 with the arterial pulse propagation delay axis. Since APPD is the measured arterial pulse propagation delay and MAP is to be calculated from the measured delay, Equation (3) can be rewritten as follows:

$$MAP = \frac{\left(\frac{APPD}{D} - APPD_{offset}\right)}{SLOPE} \quad (4)$$

For the electrode spacing described above in connection with FIG. 1, the following relationships hold for the expected range of mean arterial blood pressure for an exemplary patient:

$$APPD = 0.55 \times H (-0.875 \times MAP + 210 \text{ ms}) \quad (5)$$

and $$MAP = \frac{\left(\frac{APPD}{0.55 H} - 210 \text{ ms}\right)}{0.875} \quad (6)$$

where APPD is the arterial pulse propagation delay in milliseconds, as measured between the peaks 312 and 322 of dZ/dt waveforms 310 and 320, respectively; H is the height of the patient in meters, and MAP is the mean arterial blood pressure in torrs. The number 0.55 is the normalization factor that converts the patient's height to vascular distance. The number −0.875 is the slope of the curve 330 that has been derived from empirical measurements and has the units milliseconds/(meter·torr).

As set forth above, the relationship between the measured APPD and the mean arterial blood pressure is dependent upon the height (H) of the patient. The computational circuit is advantageously electrically connected to a data input device 340, such as a keyboard, a plurality of switches, or the like, so that the height of the patient to whom the apparatus is connected can be entered into the second computational circuit block 220 as a parameter of the calculation of Equation (6). Alternatively, the vascular distance D between the two body segments can be entered into the second computational block 220 as a parameter of the calculation of Equation (4).

The foregoing method of calculating the mean arterial blood pressure (MAP) is sufficiently accurate for most clinical purposes and generally is more accurate other conventional sphygmomanometric methods discussed above. However, the foregoing method relies upon consistent positioning of the four sensing electrodes and also presumes a distance between the two sensing segments of a patient is proportional to the patient's height. These or other factors may cause the relationship between the measured APPD and the MAP to lie on a curve that varies from the relationship shown in FIG. 3. For example, the relationship may be defined by a second curve 340 that lies above the curve 330 in FIG. 3 or by a third curve 342 that lies below the curve 240 in FIG. 3. In either case, it has been found that, within clinical accuracy, the slopes of the curves 340 and 342 are substantially the same as the slope of the curve 240 so that the curves are substantially parallel. In other words, in Equations (3) through (6), the offset time delay $APPD_{offset}$ (e.g., 210 milliseconds) would be different. If additional accuracy is required, the present invention can be calibrated by comparing the calculated mean arterial blood pressure with the pressure obtained by other methods to determine the offset time delay. The new offset time delay can then be provided as a parameter to the calculation via the data input device 340 so that the apparatus and method are calibrated for a particular patient.

In preferred embodiments of the present invention, the second computational circuit block 220 advantageously includes a microprocessor (not shown), such as a Zilog Z80, an Intel 8088, or the like that is programmed to perform the calculations described above. The second computational circuit block 220 provides an output signal on an output terminal 350 that represents the mean arterial blood pressure calculated by the second computational circuit block 210. The output signal from the output terminal 350 can be a digital value on either a serial data line or a parallel data bus. The digital value is provided as an input to a digital data device (not shown), such as a computer, which receives the MAP data and stores and analyzes the data. Alternatively, or in combination with the digital data output, the second computational circuit block includes a display device 360 which, in portable versions of the present invention, can advantageously be a digital display device such as a plurality of seven-segment display devices. The display device 360 provides a digital readout of the calculated mean arterial pressure (MAP) so that the pressure can be visually monitored by the patient or by medical personnel.

The present invention can also advantageously include a portable data storage device (not shown), such as a lowpower, non-volatile memory, to store the digital representation of the calculated mean arterial pressure while the patient is mobile. In such case, the stored data can be periodically transferred in a conventional manner to a permanent data storage device such as a floppy disk or magnetic tape.

As described above, the apparatus and method of the present invention measures the arterial pulse propagation delay and calculates the mean arterial blood pressure of the patient without using an occlusive cuff or other similar equipment that interrupts or otherwise inhibits the flow of blood to an extremity. Furthermore, the present invention can advantageously be implemented using microelectronic circuitry so that the first electrical bioimpedance measuring device 164, the second electrical bioimpedance measuring device 184, the first computational circuit 210, the second computational circuit 220, and the display device 360 can be packaged in a single/ unit so that the overall apparatus can be made very small, lightweight and self-contained. Thus, the patient can carry the unit on a belt, shoulder strap, or the like, and retain his or her mobility while the mean arterial blood pressure is continuously calculated on a beat-by-beat basis.

Referring again to FIG. 1, the circuitry of the second electrical bioimpedance measuring device 184 can be much simpler than the circuitry of the first electrical bioimpedance measuring device 164 since it is only necessary for the second electrical bioimpedance measuring device 184 to provide the second differentiated voltage output $dZ_2/dt$. Since the second differentiated voltage output $dZ_2/dt$ may have electrical noise on it that could cause the second computational circuit block 220 to prematurely detect the peak 322 of the waveform 320 of FIG. 2c. In preferred embodiments of the present invention, the second computational circuit block 220 includes a timing window that monitors the second differentiated voltage output from the second electrical bioimpedance measuring device 184 only during a range of times when the peak is expected to occur for a patient of a particular height. The timing window can be implemented, for example, in software or as a hardware timing circuit. As a specific example, consider a patient having a height of 174 centimeters. Using Equation (5), the arterial pulse propagation delay for a minimum expected MAP of 60 torr would be 150 milliseconds and the arterial pulse propagation delay for a maximum expected MAP of 150 torr would be 75 milliseconds. Thus, the second computational circuit block 220 would provide a 75 millisecond timing window that begins 75 milliseconds after detection of the peak 312 of the $dZ_1/dt$ signal and that ends 150 milliseconds after the detection of the peak 312.

DESCRIPTION OF THE METHOD OF CALCULATING LCWI AND SVRI

As set forth above, in embodiments of the invention wherein the first electrical bioimpedance measuring device 164 is an NCCOM® noninvasive continuous cardiac output monitor, or a similar device that includes the first computational circuit block 210, the first electrical bioimpedance measuring device 164 together with the first computational block 210 advantageously calculates the cardiac output (CO) of the patient on a continuous basis. The cardiac output is provided as a digital output signal on an output terminal 400 of the first computational circuit block 210. As further illustrated in FIG. 1, the output terminal 400 is advantageously electrically connected to the second computational circuit block 220 so that the digital representation of the cardiac output is provided as an input to the second computational circuit block 220. As set forth above, the cardiac index (CI) of a patient is the cardiac output (CO) of the patient normalized with respect to the patient's weight or surface area. A typical cardiac index for a healthy patient is 0.1 liters per minute of blood per kilogram of weight, or 3.4 liters per minute per square meter of body surface area. In the preferred embodiment of the present invention, the data input device 340 is also used to input the patient's weight or surface area into the second computational circuit block 220 so that the second computational circuit block can calculate the cardiac index (CI) from the cardiac output (CO). The second computational circuit block 220 uses the calculated cardiac index (CI) in combination with the calculated mean arterial pressure (MAP) to calculate the left cardiac work index (LCWI) and the systemic vascular resistance index (SVRI) on a continuous beat-by beat basis in accordance with the following equations:

$$LCWI = MAP \times CI \times 0.0144 \qquad (7)$$

and $$SVRI = (MAP/CI) \times 80 \qquad (8)$$

where MAP is the mean arterial blood pressure in torrs, CI is the cardiac index of the patient normalized for surface area (i.e., liters per minute per square meter), and 0.0144 and 80 are conversion factors for the units used for the pressure and cardiac index. The two conversion factors are different when the cardiac index is based upon weight rather than surface area. The left cardiac work index (LCWI) has the units kilogram meter per square meter (i.e., kg·m/m$^2$), and the systemic vascular resistance index (SVRI) has the units dyne seconds per cm$^5$·square meter (i.e., dyn·sec/cm$^5$·m$^2$).

Although the preferred embodiments of the present invention have been described and illustrated, it will be obvious to those skilled in the art that various changes and modifications can be made to the present invention without departing from its spirit. Accordingly, the scope of the present invention is deemed to be limited only by the scope of the following appended claims.

What is claimed is:

1. A noninvasive apparatus for continuously monitoring the means arterial blood pressure of a patient, comprising:

first electrical bioimpedance measuring means electrically connectable to a first segment of the patient's body, for sensing the increase in blood flow in the first segment caused by the ejection of blood into the arteries during the ventricular contraction of the patient's heart and for generating a first output signal that indicates when the increase in blood flow occurs in the first segment;

second electrical bioimpedance measuring means electrically connectable to a second segment of the patient's body for sensing the increase in blood flow in the second segment caused by the ejection of blood into arteries during the ventricular contraction of the patient's hear and for generating a second output signal that indicates when the increase in blood flow occurs in the second segment, the second segment located at a distance from the first segment so that the increase in blood flow in the second segment occurs at a time interval after the increase in blood flow in the first segment, said time interval between said first output signal and said second output signal proportional to the distance between the first segment and the second segment and inversely proportional to the mean arterial blood pressure of the patient; and electronic measuring and calculating means for measuring the time interval between the first output signal and the second output signal, and for calculating the means arterial blood pressure of the patient based upon the measured time interval and the distance between the first segment and the second segment.

2. The apparatus of claim 1, wherein said first electrical bioimpedance measuring means comprise:

a current source having a high-frequency constant amplitude electrical current output;

means for injecting the output of said current source into the first segment of the patient to cause current flow in said first segment;

means for sensing a voltage caused by said current flow through the first segment of the patient, said voltage having a magnitude that varies in accordance with changes in electrical bioimpedance of the first body segment caused by the flow of blood in the first body segment during each cardiac cycle; and an electronic circuit connected to said sensing means, said electronic circuit receiving said voltage sensed by said sensing means and generating a first output signal having a magnitude that changes in accordance with the blood flow in the first segment during each cardiac cycle.

3. The apparatus of claim 2, wherein said electronic circuit includes a differentiator that generates a differentiated voltage that has a magnitude proportional to the rate of change of electrical bioimpedance in the first segment, said differentiated voltage having at least one peak corresponding to the maximum rate of increase in blood flow in the first segment caused by the ventricular contraction of the patient's heart.

4. The apparatus of claim 1, wherein said second electrical bioimpedance measuring means comprise:

a current source having a high-frequency constant amplitude electrical current output;

means for injecting the output of said current source into the second segment of the patient to cause current flow in said second segment; means for sensing a voltage caused by said current flow through the second segment of the patient, said voltage having a magnitude that varies in accordance with changes in electrical bioimpedance of the second body segment caused by the flow of blood in the second body segment during each cardiac cycle; and an electronic circuit connected to said sensing means, said electronic circuit receiving said voltage sensed by said sensing means and generating a second output signal having a magnitude that changes in accordance with the blood flow in the second body segment during each cardiac cycle.

5. The apparatus of claim 4, wherein said electronic circuit includes a differentiator that generates a differentiated voltage that has a magnitude proportional to the rate of change of electrical bioimpedance in the second segment, said differentiated voltage having at least one peak corresponding to the maximum rate of increase in blood flow in the second segment caused by the ventricular contraction of the patient's heart.

6. The apparatus of claim 1, wherein said electronic measuring and calculating means comprise a microprocessor that is responsive to said first output signal from said first electrical bioimpedance measuring means and to said second output signal from said second electrical bioimpedance measuring means and that measures the time interval between the increase in blood flow indicated by said first output signal and the increase in blood flow indicated by said second output signal.

7. The apparatus of claim 6, further comprising input means electrically connected to said microprocessor for providing data input to said microprocessor representative of the distance between the first and second segments.

8. The apparatus of claim 1, wherein said electronic measuring and computing means generates an output signal that represents the mean arterial blood pressure of the patient.

9. The apparatus of claim 1, further including a display device electrically connected to said electronic measuring and computing means that displays the mean arterial blood pressure of the patient.

10. The apparatus of claim 1, wherein said electronic measuring and computing means includes a means for generating a time window that begins at a predetermined time after said increase in blood flow indicated by said first output signal and that has a predetermined duration, said electronic measuring and computing means monitoring said second output signal only during said time window to thereby reduce the probability of incorrect measurement of said time interval between the beginning of blood flow in the first segment and the beginning of blood flow in the second segment.

11. The apparatus of claim 1, wherein said electronic measuring and computing calculates the mean arterial blood pressure of the patient in accordance with the following relationship:

$$MAP = \frac{\left(\frac{APPD}{D} - APPD_{offset}\right)}{SLOPE}$$

where MAP is the calculated means arterial blood pressure, D is the vascular distance between the two body segments, APPD is the measured arterial pulse propagation delay, $APPD_{offset}$ is an empirically determined offset in the measure delay, and SLOPE is an empirically determined relationship between the change in the measured delay and the change in the mean arterial blood pressure.

12. The apparatus of claim 1, wherein said first electrical bioimpedance measuring means provides an output signal having a magnitude corresponding to the measured cardiac output of the patient, said electronic measuring and computing means converts the measured cardiac output to a magnitude corresponding to the cardiac index of the patient, and said electronic measuring and computing means calculates the left cardiac work index of the patient in accordance with the following relationship:

$$LCWI = MAP \times CI \times CONSTANT$$

where LCWI is the left cardiac work index of the patient, MAP is the mean arterial blood pressure of the patient, CI is the cardiac index of the patient, and CONSTANT is a constant selected for the parameters of the cardiac index and the pressure.

13. The apparatus of claim 1, wherein said first electrical bioimpedance measuring means provides an output signal having a magnitude corresponding to the measured cardiac output of the patient, said electronic measuring and computing circuit converts the measured cardiac output to a magnitude corresponding to the cardiac index of the patient, and said electronic measuring and computing means calculates vascular resistance index of the patient in accordance with the following relationship:

$$SVRI = (MAP/CI) \times CONSTANT$$

where SVRI is the systemic vascular resistance index of the patient, MAP is the mean arterial blood pressure of the patient, CI is the cardiac index of the patient, and CONSTANT is a constant selected for the parameters of the cardiac index and the pressure.

14. The apparatus of claim 1, wherein:
said first electrical bioimpedance measuring means comprises:
a current source having a high-frequency constant amplitude electrical current output;
means for injecting the output of said current source into the first and second segments of the patient to cause current flow in said first and second segments; first sensing means for sensing a voltage caused by current flow through the first segment of the patient, said voltage having a magnitude that varies in accordance with changes in electrical bioimpedance of the first body segment caused by the flow of blood in the first body segment during each cardiac cycle; and
a first electronic circuit connected to said first sensing means, said first electronic circuit receiving said voltage sensed by said first sensing means and generating a first output signal having a magnitude that changes in accordance with the blood flow in the first segment during each cardiac cycle;
and
said second electrical bioimpedance measuring means comprises:
second sensing means for sensing a voltage caused by current flow through the second segment of the patient, said voltage having a magnitude that varies in accordance with changes in electrical bioimpedance of the second body segment caused by the flow of blood in the second body segment during each cardiac cycle; and
a second electronic circuit connected to said second sensing means, said second electronic circuit receiving said voltage sensed by said second sensing means and generating a second output signal having a magnitude that changes in accordance with the blood flow in the second body segment during each cardiac cycle.

15. A method for noninvasively monitoring the mean arterial blood pressure of a patient, comprising:
electrically connecting a first electrical bioimpedance measuring device to a first segment of the patient's body;
sensing the increase in blood flow in the first segment caused by the ejection of blood into the arteries during the ventricular contraction of the patient's heart;
generating a first output signal that indicates when the increase in blood flow occurs in the first segment;
electrically connecting a second electrical bioimpedance measuring device to a second segment of the patient's body;
sensing the increase in blood flow in the second segment caused by the ejection of blood into the arteries during the ventricular contraction of the patient's heart;
generating a second output signal that indicates when the increase in blood flow occurs in the second segment;
locating the second segment at a distance from the first segment so that the increase in blood flow in the second segment occurs at a time interval after the increase in blood flow in the first segment, said time interval between said first output signal and said second output signal proportional to the distance between the first segment and the second segment and inversely proportional to the mean arterial blood pressure of the patient;
measuring the time interval between the first output signal and the second output signal; and
calculating the mean arterial blood pressure of the patient based upon the measured time interval and the distance between the first segment and the second segment.

16. The method of claim 15 wherein said step of sensing the blood flow in said first segment comprises the steps of:
generating a high-frequency constant amplitude electrical current;
injecting said current into the first segment of the patient;
sensing a voltage caused by current flow through the first segment of the patient, said voltage having a magnitude that varies in accordance with changes in electrical bioimpedance of the first segment caused by the flow of blood in the first segment during each cardiac cycle; and
amplifying said sensed voltage and generating a first output signal having a magnitude that changes in accordance with the blood flow in the first segment during each cardiac cycle.

17. The method of claim 16, further including the step of generating a differentiated voltage that has a magnitude proportional to the rate of change of electrical bioimpedance in the first segment, said differentiated voltage having at least one peak corresponding to the maximum rate of increase in blood flow in the first segment caused by the ventricular contraction of the patient's heart.

18. The method of claim 15, wherein said step of sensing the blood flow in said second segment comprises the steps of:
   generating a high-frequency constant amplitude electrical current;
   injecting said current into the second segment of the patient;
   sensing a voltage caused by current flow through the second segment of the patient, said voltage having a magnitude that varies in accordance with changes in electrical bioimpedance of the second segment caused by the flow of blood in the second segment during each cardiac cycle; and
   amplifying said sensed voltage and generating a second output signal having a magnitude that changes in accordance with the blood flow in the first segment during each cardiac cycle.

19. The method of claim 18, further including the step of generating a differentiated voltage that has a magnitude proportional to the rate of change of electrical bioimpedance in the first segment, said differentiated voltage having at least one peak corresponding to the maximum rate of increase in blood flow in the second segment caused by the ventricular contraction of the patient's heart.

20. The method of claim 15, wherein said calculating step is performed by a microprocessor and further including the step of inputting data to said microprocessor representative of the distance between the first and second segments.

21. The method of claim 15, further including the step of generating an output signal that represents the mean arterial blood pressure of the patient.

22. The method of claim 15, further including the displaying the mean arterial blood pressure of the patient.

23. The method of claim 15, further including the step of generating a time window that begins at a predetermined time after said increase in blood flow indicated by said first output signal and that has a predetermined duration, said measuring step operational to measure the end of said time interval only during said time window to thereby reduce the probability of incorrect measurement of said time interval between the beginning of blood flow in the first segment and the beginning of blood flow in the second segment.

24. The method of claim 15, wherein said calculating step is performed in accordance with the following relationship:

$$MAP = \frac{\left(\frac{APPD}{D} - APPD_{offset}\right)}{SLOPE}$$

where MAP is the calculated mean arterial blood pressure, D is the vascular distance between the two segments, APPD is the measured arterial pulse propagation delay, $APPD_{offset}$ is an empirically determined offset in the measure delay, and SLOPE is an empirically determined relationship between the change in the measured delay and the change in the mean arterial blood pressure.

25. The method of claim 24, wherein SLOPE is approximately −0.875 milliseconds per meter per torr and $APPD_{offset}$ is approximately 210 milliseconds.

26. The method of claim 15, further including the steps of:
   providing an output signal having a magnitude corresponding to the measured cardiac output of the patient;
   converting the measured cardiac output to a magnitude corresponding to the cardiac index of the patient; and
   calculating the left cardiac work index of the patient in accordance with the following relationship:

$$LCWI = MAP \times CI \times CONSTANT$$

where LCWI is the left cardiac work index of the patient, MAP is the mean arterial blood pressure of the patient, CI is the cardiac index of the patient, and CONSTANT is a constant selected for the parameters of the cardiac index and the pressure.

27. The method of claim 15, further including the steps of:
   providing an output signal having a magnitude corresponding to the measured cardiac output of the patient;
   converting the measured cardiac output to a magnitude corresponding to the cardiac index of the patient; and
   calculating the systemic vascular resistance index of the patient in accordance with the following relationship:

$$SVRI = (MAP/CI) \times CONSTANT$$

where SVRI is the systemic vascular resistance index of the patient, MAP is the mean arterial blood pressure of the patient, CI is the cardiac index of the patient, and CONSTANT is a constant selected for the parameters of the cardiac index and the pressure.

* * * * *